United States Patent [19]

Koeneman et al.

[11] Patent Number: 4,895,573

[45] Date of Patent: Jan. 23, 1990

[54] FEMORAL-JOINT PROSTHETIC DEVICE

[75] Inventors: James B. Koeneman, Mesa; Joseph A. Longo, Phoenix; Roger H. Johnson, Phoenix; Thomas M. Hansen, Phoenix; Allan M. Weinstein, Paradise Valley; Thomas P. Murray, Scottsdale, all of Ariz.

[73] Assignee: Harrington Arthritis Research Center, Phoenix, Ariz.

[21] Appl. No.: 172,026

[22] Filed: Mar. 23, 1988

Related U.S. Application Data

[62] Division of Ser. No. 753,711, Jul. 10, 1985, Pat. No. 4,738,681.

[51] Int. Cl.$^4$ .............................. A61F 2/36; A61F 2/32
[52] U.S. Cl. ........................................... 623/23; 606/89
[58] Field of Search ..................... 623/22, 23, 16, 66; 128/92 VJ, 92 VV, 92 V

[56] References Cited

U.S. PATENT DOCUMENTS

| | | | |
|---|---|---|---|
| 4,101,985 | 7/1978 | Baumann et al. | 3/1.912 |
| 4,146,936 | 4/1979 | Aoyagi et al. | 3/1.91 |
| 4,221,623 | 9/1980 | Heissler et al. | 156/169 |
| 4,459,708 | 7/1984 | Buttazzoni | 3/1.91 |
| 4,506,393 | 3/1985 | Murphy | 3/1 |
| 4,530,114 | 7/1985 | Tepic | 623/23 |
| 4,546,501 | 10/1985 | Gustilo et al. | 623/22 X |
| 4,552,136 | 11/1985 | Kenna | 128/92 VJ |
| 4,589,883 | 5/1986 | Kenna | 623/22 |
| 4,650,489 | 3/1987 | Thompson | 623/16 |
| 4,657,551 | 4/1987 | Ecke | 623/23 |
| 4,657,552 | 4/1987 | Karpf | 623/23 |
| 4,662,887 | 5/1987 | Turner et al. | 623/16 |

FOREIGN PATENT DOCUMENTS 3247726 6/1984 Fed. Rep. of Germany .

OTHER PUBLICATIONS

Mathys et al, "The Use of Polymers for Endoprosthetic Components", pp. 71-80 of The Cementless Fixation of Hip Endoprosthesis, Mosher ed., Springer-Verlag (1984).
Bombelli et al, The Hip, 12, pp. 133-145 (1984).
Grays Anatomy, pp. 188-189, 1901 ed., Running Press, Philadelphia, PA.
Harty, "The Calcar Femorale and the Femoral Neck", J. Bone and Joint Surgery, 39A, pp. 625-630 (1957).
Griffin, "The Calcar Femorale Redefined", Clin. Orthoped and Related Research, No. 164, (1982).

*Primary Examiner*—Richard J. Apley
*Assistant Examiner*—Alan W. Cannon
*Attorney, Agent, or Firm*—Vidas & Arrett

[57] ABSTRACT

A femoral-side hip-joint prosthetic device for use in hip-joint replacement. The device includes an elongate stem whose surface defines maximally spaced inferomedial and supero-lateral surface curves, and which is characterized by a surface rotation which carries the supero-lateral surface curve about 15°-30° forward with respect to the infero-medial surface curve, on progressing upward along the upper surface portion of the stem, with the device in operative position. The rotation of the stem surface produces a close approximation to the cavity formed in the proximal femur by removal of the cancellous bone in the natural cavity formed by a wall of densified cancellous bone. A 3°-15° proximal anteversion of the neck is adapted to place a hip-joint ball carried on the stem at a position closely approximating that of the head in the natural femur. In the method of the invention, the cavity which receives the prosthesis stem is formed by a rasp/broach-type tool whose surface conforms closely to that of the stem.

4 Claims, 2 Drawing Sheets

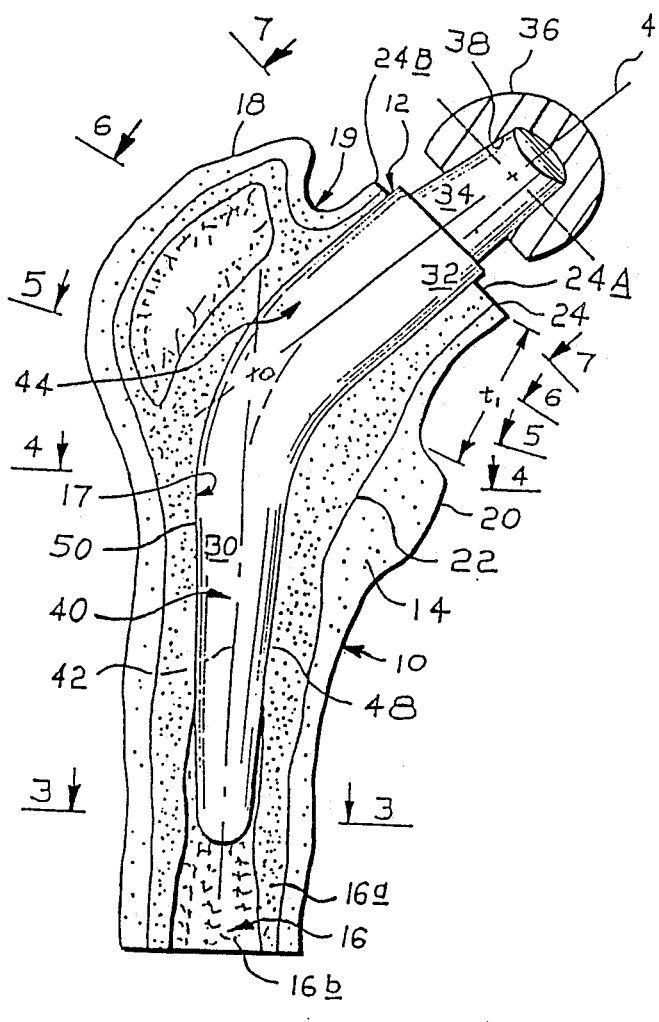
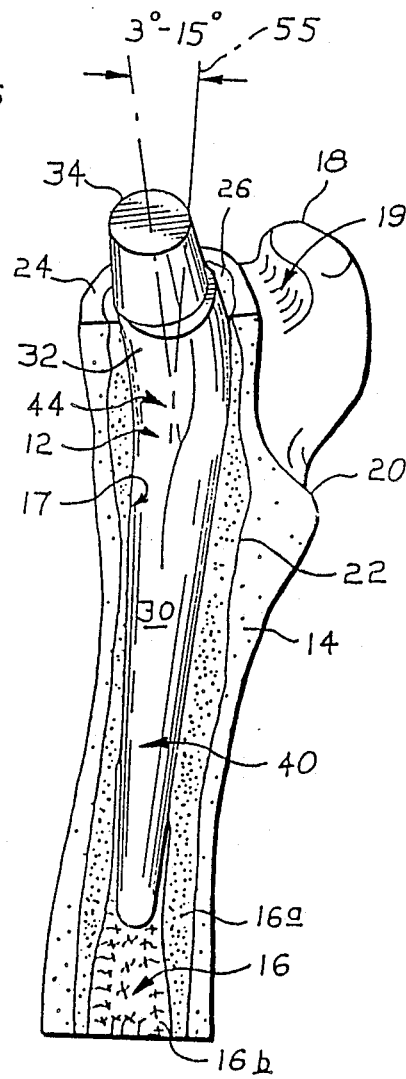

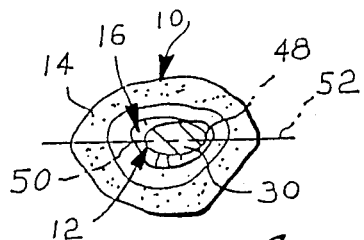
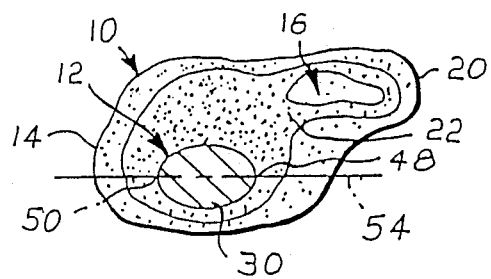
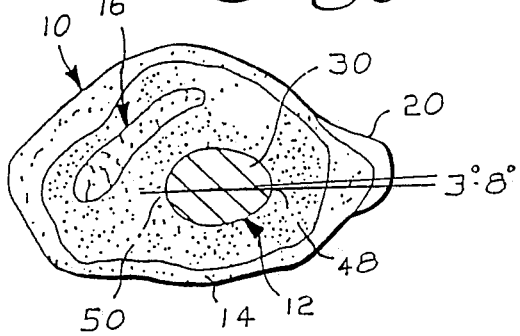
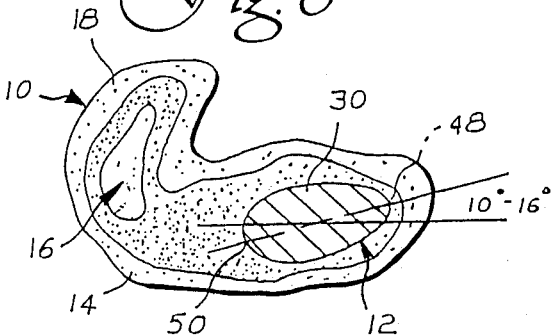
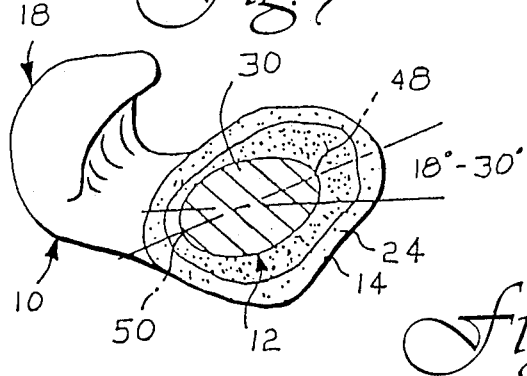
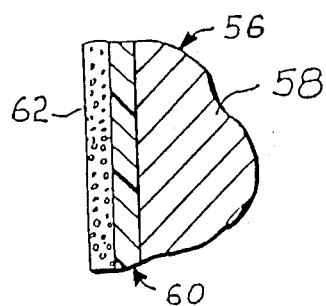
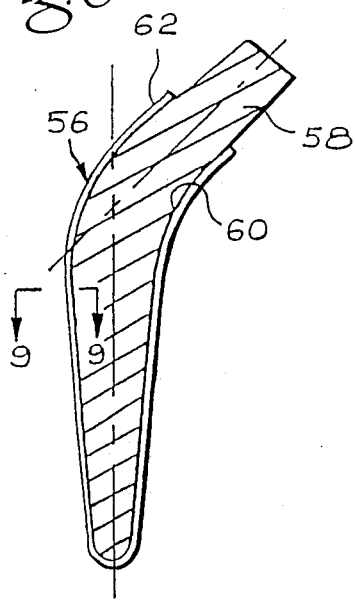

FEMORAL-JOINT PROSTHETIC DEVICE

This is a divisional of co-pending application Ser. No. 753,711 filed on July 10, 1985, now U.S. Pat. No. 4,738,681.

FIELD OF THE INVENTION

The present invention relates to a femoral-side hip-joint prosthetic device.

BACKGROUND OF THE INVENTION

Hip-joint replacement is a widely used orthopedic procedure to correct various types of hip joint injury, such as those caused by osteoarthritis, fracture dislocations, rheumatoid arthritis, and aseptic bone necrosis. A femoral-side hip-joint prosthesis typically includes, in basic design, an elongate stem which is adapted for receipt in a cavity formed in the proximal region of the femur, and a ball-like hip-joint member carried at the upper end of the stem. To attach the prosthesis to the femur surgically, the head of the femur is removed, and the internal bone region below the cut is removed to form the cavity which will receive the prosthesis stem. The stem may be anchored in the cavity by a cementitious material such as polymethylmethacrylate (PMMA), which acts as a grout material, by bonding directly to bone, such as with hydroxyapatite and/or by biological fixation, such as by bone growth into a porous surface of the stem.

Heretofore, femoral-side hip-joint replacement has not been entirely satisfactory, particularly in active younger patients, where it is important to form a stable, long-lasting prosthetic attachment. The stem size and shape in prior art hip-joint prostheses has generally required removal of a substantial amount of hard outer cortical bone in forming a cavity which can accommodate the stem. This removal alters the load distribution within the bone, which can lead to detrimental long-term bone remodeling. Also, in the surgical technique required in prior art prostheses, the piriformis fossa is substantially reamed, and this compromises the blood supply to the proximal femur. Also, the natural iternal support canal which is formed by dense cancellous bone is removed in order to insert prior art prostheses.

A second limitation is related to the manner in which prior-art stems are anchored in the cavity. In order to permit stem receipt in the cavity, a large amount of proximal femur must be removed. This requires a relatively large prosthesis cross-section to achieve good bone/prosthesis apposition.

Attempts to anchor a prosthesis stem by press fit in a cavity, typically using a three-point fixation system have often failed to produce stable fixation, due to stem loosening because of torsion or breakdown of the three point support system.

SUMMARY OF THE INVENTION

It is one general object of the invention to provide a femoral-side hip-joint prosthetic device which substantially solves or overcomes the above-mentioned problems associated with the prior art.

A related object of the invention is to provide, in such a device, an elongate stem sized and dimensioned to conform to a natural intramedullary space in the proximal femur.

Another object of the invention is to provide a joint replacement device whose stem is adapted to be received relatively snugly, and by a twist-in action, in a bone cavity, to promote stable biological fixation to the bone and/or to allow press-fit attachment of the device to the bone.

In one embodiment, the prosthetic device of the invention includes a stem whose outer surface defines maximally spaced infero-medial and supero-lateral surface curves, and which is characterized by a surface rotation which carries the supero-lateral curve about 15°–30° forward with respect to the infero-medial curve, on progressing upward along a proximal portion of the stem, with the device in operative position. This surface configuration conforms substantially to the intramedullary cavity formed by removing only the less dense cancellous bone material from the proximal femur. A neck mounted on the proximal end of the stem is adapted to support the head of a ball-type hip joint. The device may have a 3°–15° anteversion of the neck.

The stem may have layered construction formed of an inner composite core having an elastic modulus less than about $20 \times 10^6$ psi, and an outer composite sheath having an elastic modulus less than that of bone. The core is adapted to carry most of the bending load, and the sheath, most of the torsional load. The design provides a relatively low-stiffness prosthesis which allows good load transfer from the prosthesis to the bone and adequate bending strength. The stem construction may also include an outer fixation layer allowing for a biological attachment of the device to the bone.

In the method for surgically implanting the prosthetic device in a proximal femur, the less dense cancellous material of the bone is removed with a rasp/broach-like instrument whose surface shape and dimensions are substantially like those of the stem. The cavity produced is adapted to receive the stem by a slight twist-in movement which seats the stem with multiple proximal contact areas in a press-fit fashion within the cavity. The stem is preferably bonded to the bone by a biological fixation, which may involve bonding to a microporous surface or to a surface-bound hydroxyapatite or other suitable bioactive material in the proximal stem region, or by press fit.

In a more general embodiment, the prosthesis of the invention includes a stem having a surface twist which provides a twist-type interlock between stem and bone, when the stem is inserted into a complementary shaped cavity formed in the bone.

These and other objects and features of the present invention will become more fully apparent when the following detailed description of the invention is read in conjunction with the accompanying drawings.

BRIEF DESCRIPTION OF THE DRAWINGS

FIG. 1 is a frontal sectional view of a proximal portion of a right femur fitted with a prosthetic device constructed according to an embodiment of the invention;

FIG. 2 is a side sectional view of the femur and attached prosthetic device, as viewed from the right in FIG. 1, and with the ball-joint member removed;

FIGS. 3–7 show a series of cross-sections taken along lines 3—3, 4—4, 5—5, 6—6, and 7—7, respectively in FIG. 1;

FIG. 8 is a side-sectional view of a prosthetic device having a layered construction; and FIG. 9 shows an enlarged cross-sectional view of a layered region of the prosthetic device from FIG. 8.

DETAILED DESCRIPTION OF THE INVENTION

FIG. 1 shows, in frontal sectional view, the proximal (upper end) portion of a human right femur 10 and an attached prosthesis device 12 constructed according to the present invention. The femur and attached device are seen in side sectional view in FIG. 2, as viewed from the right in FIG. 1.

The femur is composed of an outer cortex or shell 14 formed of hard cortical material, and a honeycomb-like internal structure 16 which fills the proximal end of the region of the bone is composed of densified cancellous material, indicated at 16a in FIGS. 1 and 2, and a less dense cancellous material 16b (indicated by wavy lines in these figures).

The densified cancellous material defines a spiraled intramedullary cavity 17 whose surface-wall features will be discussed below. Cavity 17 is also referred to herein as a pseudo-intramedullary cavity to distinguish it from a larger intramedullary cavity defined substantially by cortical-shell surfaces of the bone.

The femur has two distinctive surface features—a greater trochanter 18, seen prominently in FIG. 1, and a lesser trochanter 20, on the posterior side of the bone, seen particularly in FIGS. 1, 2, 5, and 6. Formed in the internal cancellous bone structure is a dense-material plate or calcar femorale, which covers the lesser trochanter from within. The calcar femorale is indicated at 22 in FIGS. 1, 2, and 4. Also of note is a densification of the cancellous bone separating the greater trochanter and the pseudo-intramedullary canal. The reader is referred to Garden, R. S., et al, J Bone and Joint Surg (1961) 43B(3): 576, for a more detailed description of the proximal femur construction, and particularly the arrangement of the cancellous bone material which forms structure 16. As brought out in this reference, the proximal end of the femur is partially spiraled, presumably reflecting the developmental response of the femur to an upright position, where weight loading occurs along a vertical direction.

The bone has been cut surgically along a plane 24 approximately normal to the axis of the neck of the femur, providing an opening 26—seen partially in FIG. 2—for cavity 17, in which device 12 is received. With reference to FIG. 1, the plane of cut extends from a lower region 24A spaced in a distance $t_1$ above the maximal projection of the lower trochanter, as indicated, to an upper region 24B that is medial to the medial border of the piriformis fossa (the notched region seen at 19 in FIG. 1). For reasons which will be seen below, the construction and configuration of the device allows the surgical cut to be made at the subcapital level with a minimal loss of upper bone stock. In particular, $t_1$ is characteristically 4-10 mm longer than the comparable neck-cut distance associated with prior art hip-prosthetic devices, and the piriformis fossa is kept substantially intact.

With continued reference to FIGS. 1 and 2, device 12 includes an elongate stem 30 which terminates at a proximal neck 32, and a tapered thimble 34, formed integrally with the stem on the neck. Thimble 34 is adapted to carry a hip-joint head, or member 36, which is received by press fit in a tapered cavity 38 formed in the member. The thimble and cavity may have various complementary configurations, e.g., elliptical, to prevent the member from rotating on the thimble.

A distal portion 40 of the stem defines a central axis 42 which substantially parallels the long axis of the bone, with the device in operative position. An upper or proximal curved stem portion 44 defines, with the thimble 34, a central axis 46 which meets axis 42 at an angle $\theta$ in FIG. 1. Angle $\theta$ is preferably between 125° and 155°.

The surface of the stem, as viewed in FIG. 1, has maximally spaced infero-medial and supero-lateral surface curves 48, 50, respectively, extending along the length of the stem. According to an important feature of the invention, the surface of the stem is characterized by a surface rotation which carries supero-lateral curve 50 between about 15°-30° forward (in an anterior direction with the device in operative position) with respect to infero-medial curve 48, on moving upward along the stem's proximal portion.

The stem surface configuration just described can be appreciated particularly with reference to FIGS. 3-7, which show a series of cross-sections taken at increasingly more proximal regions along the bone. In FIG. 3, it is seen that the lower distal portion of the stem has a substantially elliptical cross-section, in which the minor axis is shifted laterally somewhat from the mid-point of the major axis. The major axis of the elliptical cross-section, indicated at 52 in FIG. 3, extends in a substantially side-to-side direction with respect to the bone's body orientation, and intersects the stem surface at curves 48, 50. The FIG. 4 sectional view shows the increase in area of the cross-sectional of the stem on moving upward along the distal stem portion. The major axis, defined by the elliptical cross-section in FIG. 4 and indicated at 54, substantially parallels axis 52.

The elliptical twist in the stem surface, on moving upward along the stem's proximal portion, can be appreciated from FIGS. 5-7. Looking first at FIG. 5, it is seen that the modified elliptical cross-section of the stem has between about 3°-8° rotation, as defined by the angle between the major axes of the elliptical cross-sections in FIGS. 3 and 4 and the major axis of the elliptical cross-section in FIG. 5. The rotation or twist in the elliptical cross-section increases to between about 10°-16° at the level of section line 6—6, and increases further to a maximum of about 30° at the proximal end of the stem corresponding to section line 7—7, and seen in FIG. 7. The twist in the surface, which has been described as a rotation of the major axes of the elliptical cross-sections on progressing upward, corresponds to a movement of supero-lateral surface curve 50 between about 15°-30°, suitably 18°-30°, forward with respect to the infero-medial curve 48. The surface-twist geometry of the stem necessitates a right and left prosthesis, because the rotation of the prosthesis cross-section on one side is counterclockwise and on the other is clockwise.

With reference now to FIG. 2, the stem's neck and the attached thimble are inclined about 3°-15° forward (toward the anterior of the body) with respect to an axis 55 which extends through the stem's lower proximal region, parallel to axis 42. This inclination, or anteversion, functions to place ball member 36 at a position which closely approximates the average position occupied by the natural head in the femur. It is noted, however, that actual variations in the head positions in a large population range from about 38° anteversion to 20° retroversion. In cases of more extreme retroversion, it may be advantageous to incline the thimble (and attached ball member) in a more neutral position.

The prosthetic device of the invention may be constructed of a variety of biocompatible metals, metal alloys, and/or composite materials which provide suitable strength and other elastic mechanical characteristics. The bending stiffness of the material is affected by its modulus of elasticity, defined as the slope of the linear portion of the stress-strain curve. All orthopedic stem materials have considerably larger moduli of elasticity than bone, whose modulus value is about $2-3 \times 10^6$ psi, but it is desired to avoid materials such as stainless steel or cobalt-chromium alloys, which have a modulus of elasticity values greater than about $28 \times 10^6$ psi. One preferred orthopedic material is a titanium alloy whose modulus of elasticity value is about $16 \times 10^6$ to $18 \times 10^6$ psi. The stem may be provided with a microporous surface, according to known fabricating techniques, or coated with a layer of hydroxyapatite or other suitable bioactive material.

Another preferred stem material is a composite composed of graphite or other high-strength fibers in a polymer matrix. The composite material has a relatively low elastic modulus, in the range between about $15-20 \times 10^6$ psi in a longitudinal direction, and moduli which are considerably lower—in the range of 1 to $2 \times 10^6$ psi—in a direction transverse to the fiber direction. A composite composed of unidirectional fibers also has a low torsional stiffness along the axis of the fibers.

The stem is also preferably constructed to accommodate torsional loads without imparting a high stress to the interface bonding between the stem and the bone. This capability may be especially important where the stem is attached to the bone, in its proximal region, by biological fixation. FIG. 8 shows a sectional view of a novel layered stem construction that combines the high strength and favorable bending characteristics of a composite material with relatively low torsional response characteristics. The stem, which is indicated generally at 56, includes an inner composite core 58 composed of unidirectional graphite or other high-strength fiber in a polymer matrix. Surrounding the core is sheath 60 of braided, woven, or plied fibers in a polymer matrix. The sheath is designed to carry most of the torsional loads transferred to the stem from the hip joint. The thickness of the sheath can be varied typically between about 0.02 and 0.30 inches, depending on the desired relative contributions of the sheath and core to bending stiffness and resistance to torsional loads. The proximal region of the sheath may be covered by an outer surface coating 62 of a bonding material, such as particles of hydroxyapatite or other bioactive material embedded in a polymer. The core, sheath, and outer coating layers are shown in fragmentary, expanded scale in FIG. 9.

The construction just described provides a comparatively low-stiffness prosthesis which allows good load transfer from the stem to the bone and yet has high strength, relatively small size, and the capability of accommodating torsional loads.

The procedure for inserting device 12 to a proximal femur, according to the method of the invention, will now be described. Initially, the bone is cut surgically at the subcapital level along plane 24 to remove the femur head which is to be replaced. The distance $t_1$ used in gauging the plane of cut will vary somewhat depending on the size of bone being cut. However, the principle is to preserve the maximal amount of proximal femur. The region of cut is generally similar to that illustrated in FIG. 1.

To form cavity 26 there is provided, according to the method of the invention, a rasp/broach tool (not shown) having substantially the same shape and size as the stem of the device which is to be inserted. In particular, the rasp has a surface twist and may have a slight anteversion in the "proximal" region of the tool corresponding to the surface features of the corresponding stem. Here it is noted that, in order to cover the wide range of bone sizes which are encountered in orthopedic surgery, it may be necessary to have as many as six or seven sizes of prosthetic devices, and a corresponding number of rasp/broach tools for use with each of the different-size prosthetic devices. In selecting an optimal stem size for a particular bone, it is generally desirable to select the largest stem size which can be received in a cavity formed by removal of cancellous bone material within the pseudo-intramedullary space only. This size selection can be made accurately from X-rays of the proximal femur.

The selected-size rasp is used to remove portions of the cancellous-bone structure 16 to form a cavity whose size and shape are dimensioned to conform substantially to the surface of the stem. The elliptical-twist surface feature in the rasp/broach requires that the tool be worked with a slight twisting movement as it is moved in and out of the cavity region. The resultant cavity has a 15°-30° surface twist (depending on the surface twist of the tool) which, in effect, optimizes the size of the stem which can be received in the cavity without (a) making a substantially more distal cut in the femur, (b) removing hard cortical bone material and portions of the calcar femorale, and/or (c) violating the denser cancellous bone which form the boundary of the pseudo-intramedullary space. Also, no extra bone is removed by rasping, so that with the final fit, no gaps remain between the prosthesis and bone.

The stem is now inserted into the cavity, using a slight twisting movement as the stem is moved fully into the cavity, to seat the stem with a large surface-contact fit into the cavity. The stem may be held in the cavity in the bone either using a grout material, such a PMMA, or preferably by biological fixation along the stem's proximal portion, where the stem has a microporous surface or is coated with hydroxyapatite particles or other bioactive material in a polymer matrix. Alternatively, the stem may be anchored in the bone by simple press fit, i.e., without provision for bonding of the stem to the bone.

From the foregoing, it can be appreciated how various objects and features of the invention are met. The device includes a stem whose novel geometry and surface features minimize the amount of bone stock which must be removed to insert and stabilize the prosthesis in the bone cavity. Specifically, by fashioning the stem to conform substantially to the soft cancellous region of the proximal femur, the stem cavity can be formed with a minimum loss of hard bone material, as compared with a stem configuration that does not follow the natural spiral of the bone. In particular, both a higher neck cut can be made and less internal cortical and dense cancellous type material needs to be removed.

The twist-in feature of stem insertion into the cavity acts to seat the stem within the cavity, essentially preventing the stem from further twisting, as tends to occur in conventional types of hip-joint prosthetic devices. This interlock allows the stem to be attached by press-fit only—i.e., without the use of cement or biological fixation—with a minimum risk that the stem will be able to work loose in the cavity with continued bending and torsional loads. Where the stem is anchored by biological fixation, the interlock feature acts to hold the stem in an immobilized state during the several-month period in which biological fixation is occurring, and the patient may therefore enjoy greater freedom of leg movement during this period.

The surface-twist feature described above provides a stable configuration which is applicable to stem fixation into any bone having an elongate intramedullary canal—e.g., tibia, humerus, ulna, metacarpals, phalanges. In this more general application, the invention includes an elongate stem having proximal and distal ends, and an outer surface which defines a pair of maximally spaced surface curves extending along the length of the stem. The stem surface is characterized by a twist in the surface curves on progressing toward the articulating surface of the bone which is being replaced. That is, the orientation of the axes which intersect and are substantially normal to the two curves shifts in either a clockwise or counterclockwise direction, when viewed down the long axis of the stem. The degree of twist in the stem is preferably between about 15 and 45 degrees. The stem is adapted for receipt by a twist-on motion within a substantially complementary-shaped cavity formed in an end region of a bone. Also included in the device is structure carried on the proximal end of the stem for supporting a replacement joint. The structure may include a neck, as in prosthetic device 12, for receiving a detachable joint member, or the joint member may be integrally formed with the stem through suitable support structure.

A preferred stem construction in the invention comprises a layered core/sheath construction which provides advantages of (a) relatively low bending stiffness, (b) high strength, (c) low torsional resistance, and (d) relatively small size. The low elastic modulus, to the extent that it more closely approximates the low elastic modulus of the bone, provides for less stress protection and more efficient load transfer between the prosthesis and the bone.

While preferred embodiments of the invention have been described herein, it will be apparent that various changes and modifications can be made without departing from the spirit of the invention. For example, although the stem in the prosthetic device illustrated in the figures has a modified elliptical cross-sectional shape, other elongate cross-sectional configurations, such as one having a series of substantially planar faces, are compatible with the stem surface features described herein.

It is claimed:

1. A method of replacing the hip joint in a femur, comprising:
   cutting the femur to remove the head portion thereof,
   removing relatively soft cancellous bone material below the cut to form an elongate intramedullary cavity defined substantially by a wall of densified cancellous bone contained within the cortical shell in the proximal end of a femur whose surface has 15°–30° twist in a proximal end region on progressing toward the proximal femur end, said wall covering the greater and lesser trochanters from within and including the calcar femorale,
   providing a femoral hip-joint prosthetic device having a stem which substantially conforms in shape and dimensions to such cavity, and
   inserting the stem into the cavity, with a twist-in motion, until the stem is received by press fit in the cavity.

2. The method of claim 1, wherein said removing includes providing a rasp/broach having substantially the same size and shape of such stem, and using the rasp/broach to remove such cancellous bone region.

3. The method of claim 1 wherein said femur cut is made along a plane approximately normal to the axis of the neck at a subcapital position which leaves the piriformis fossa substantially intact.

4. The method of claim 1 wherein said cavity surface twist is 18°–30°.

* * * * *